United States Patent
Grubbs et al.

(10) Patent No.: US 11,682,319 B2
(45) Date of Patent: Jun. 20, 2023

(54) FAKE BLOOD FOR USE IN SIMULATED SURGICAL PROCEDURES

(71) Applicant: Intuitive Surgical Operations, Inc., Sunnyvale, CA (US)

(72) Inventors: W. Andrew Grubbs, Sunnyvale, CA (US); John Alexander, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 442 days.

(21) Appl. No.: 16/486,314

(22) PCT Filed: Feb. 17, 2017

(86) PCT No.: PCT/US2017/018286
§ 371 (c)(1),
(2) Date: Aug. 15, 2019

(87) PCT Pub. No.: WO2017/155678
PCT Pub. Date: Sep. 14, 2017

(65) Prior Publication Data
US 2020/0005679 A1 Jan. 2, 2020

(51) Int. Cl.
G09B 23/30 (2006.01)
A61B 34/30 (2016.01)
G09B 23/28 (2006.01)

(52) U.S. Cl.
CPC ............ G09B 23/303 (2013.01); A61B 34/30 (2016.02); G09B 23/285 (2013.01)

(58) Field of Classification Search
CPC ....... G09B 23/28; G09B 23/30; G09B 23/303
See application file for complete search history.

(56) References Cited

U.S. PATENT DOCUMENTS

| | | | |
|---|---|---|---|
| 2,220,099 A | 11/1940 | Guenther et al. | |
| 2,477,383 A | 7/1949 | Lewis | |
| 4,483,779 A | 11/1984 | Llenado | |
| 4,483,780 A | 11/1984 | Llendado | |
| 4,565,647 A | 1/1986 | Llenado | |
| 5,055,259 A * | 10/1991 | Inoue | G09B 19/00 422/430 |
| 5,332,528 A | 7/1994 | Pan et al. | |
| 5,792,135 A | 8/1998 | Madhani et al. | |
| 5,817,084 A | 10/1998 | Jensen | |
| 6,004,918 A * | 12/1999 | Adams | C11D 3/0026 510/337 |
| 6,008,181 A | 12/1999 | Cripe et al. | |
| 6,020,303 A | 2/2000 | Cripe et al. | |
| 6,060,443 A | 5/2000 | Cripe et al. | |
| 6,093,856 A | 7/2000 | Cripe et al. | |
| 6,153,577 A | 11/2000 | Cripe et al. | |
| 6,331,181 B1 | 12/2001 | Tierney et al. | |
| 6,441,577 B2 | 8/2002 | Blumenkranz et al. | |
| 6,482,994 B2 | 11/2002 | Scheper et al. | |
| 6,491,701 B2 | 12/2002 | Tierney et al. | |
| 6,521,586 B1 | 2/2003 | Hoogland et al. | |
| 6,521,587 B1 | 2/2003 | L'Hostis et al. | |
| 6,790,043 B2 * | 9/2004 | Aboud | G09B 23/303 434/262 |
| 6,817,974 B2 | 11/2004 | Cooper et al. | |
| 6,824,389 B1 * | 11/2004 | Garrett, Jr. | G09B 23/306 434/262 |
| 7,618,821 B2 * | 11/2009 | Ryan | G01N 33/96 422/73 |
| 7,659,372 B2 * | 2/2010 | Hood | A61K 38/014 530/354 |
| 7,963,913 B2 | 6/2011 | Devengenzo et al. | |
| 9,542,861 B2 * | 1/2017 | Day | A61K 33/14 |
| 2005/0202381 A1 * | 9/2005 | Keegan | G09B 23/286 434/262 |
| 2005/0239908 A1 | 10/2005 | Creutz et al. | |
| 2007/0167315 A1 | 7/2007 | Arriola et al. | |
| 2007/0243512 A1 * | 10/2007 | King | G09B 23/30 434/268 |
| 2008/0021152 A1 | 1/2008 | Rautschek et al. | |
| 2009/0011394 A1 * | 1/2009 | Meglan | G09B 23/28 434/268 |
| 2011/0200977 A1 * | 8/2011 | Paronen | G09B 23/285 434/268 |
| 2013/0224712 A1 * | 8/2013 | Day | A61K 35/14 434/268 |
| 2013/0330700 A1 | 12/2013 | Feins et al. | |
| 2015/0024362 A1 | 1/2015 | Feins et al. | |
| 2015/0140537 A1 * | 5/2015 | Grinevich | G09B 23/303 434/262 |
| 2016/0140878 A1 * | 5/2016 | Fernandez | A01N 1/00 434/268 |
| 2016/0165880 A1 * | 6/2016 | Tsukiyama | A01N 1/0247 435/284.1 |
| 2019/0033419 A1 * | 1/2019 | Golay | G01R 33/58 |
| 2020/0165393 A1 * | 5/2020 | Rautschek | C11D 3/0026 |

FOREIGN PATENT DOCUMENTS

| | | |
|---|---|---|
| RU | 2045902 | 10/1995 |
| WO | 9206162 | 4/1992 |
| WO | 9319038 | 9/1993 |
| WO | 9319146 | 9/1993 |
| WO | 9409099 | 4/1994 |
| WO | 9905082 | 2/1999 |
| WO | 9905084 | 2/1999 |
| WO | 9905241 | 2/1999 |
| WO | 9905242 | 2/1999 |

(Continued)

OTHER PUBLICATIONS

"Fake Blood Recipe", Oct. 21, 2013 (viewable at https://www.youtube.com/watch?v=D-rQzrNinS4). (Year: 2013).*

(Continued)

*Primary Examiner* — Kurt Fernstrom
(74) *Attorney, Agent, or Firm* — Allen, Dyer, Doppelt + Gilchrist, P.A.

(57) ABSTRACT

Artificial blood compositions for use in simulated surgery, and kits including the compositions, are disclosed. Tissues, organs, and organ blocks which include dissolvable clots are also disclosed. Further disclosed are methods for carrying out simulated surgical procedures using the compositions, tissues, organs, organ blocks, and kits described herein.

3 Claims, No Drawings

(56) References Cited

FOREIGN PATENT DOCUMENTS

| WO | 9905243 | 2/1999 |
| WO | 9905244 | 2/1999 |
| WO | 9907656 | 2/1999 |
| WO | 0023548 | 4/2000 |
| WO | 0023549 | 4/2000 |
| WO | 0142408 | 6/2001 |
| WO | 2007008776 | 1/2007 |
| WO | 2007074326 | 7/2007 |

OTHER PUBLICATIONS

Bulanov, Yu.A., et al. The protocol for the treatment of acute blood loss: the main provisions. Bulletin of Intensive Care, 2004, N25, pp. 193-195.
International Preliminary Report on Patentability for Application No. PCT/US2017/018286, dated Aug. 29, 2019, 6 pages.
International Search Report and Written Opinion for Application No. PCT/US2017/018286, dated Jul. 6, 2017, 7 pages.
Small Medical Encyclopedia, Moscow, Publishing House "Soviet Encyclopedia," 1991, vol. 2, pp. 555-559-pp. 555, 558-559.
Mashkovsky M.D., Medicines. A guide for doctors. 16th edition, Moskov, "NewWave", Publisher Umerenkov, 2012, pp. 1-14. (Machine Translated).

* cited by examiner

FAKE BLOOD FOR USE IN SIMULATED SURGICAL PROCEDURES

FIELD OF THE INVENTION

The present invention relates to the field of fake blood formulations for use in simulated surgical procedures, such as those performed on a surgical simulator rather than on a live human or animal.

BACKGROUND

Historically, surgery has been performed by making relatively large incisions in a patient to access a surgical site. More recently, robotic surgery allows a surgeon to perform procedures through relatively small incisions. The surgeon passes an endoscope through a small incision, and the endoscope includes a camera that allows the surgeon to view the patient's internal organs. Robotic procedures tend to be less traumatic, and to have shorter recovery times, than conventional surgical procedures.

Representative examples of procedures that can be performed using robotic surgery include heart surgery, lung surgery, prostate surgery, hysterectomies, joint surgery, and back surgery. Companies like Intuitive Surgical, Inc. ("Intuitive") provide robotic systems that allows surgeons to perform minimally invasive surgery, including coronary artery by-pass grafting (CABG) procedures. The procedures are performed with instruments that are inserted through small incisions in the patient's chest, and controlled by robotic arms. The surgeon controls the movement of the arms, and actuates "effectors" at the end of the arms using handles and foot pedals, which are typically coupled to electronic controllers. Recent advances allow the surgeon to use voice commands, or "line-of-sight," to control the movement of the endoscope and other robotic arms. Further, the surgeon can "feel" the force applied to the tissue, so as to better control the robotic arms.

In addition to using an endoscope to view the surgical site, the surgeon can use a laser or scalpel to cut tissue, an electrocautery device to cauterize tissue, a "grabber" to grab tissue, such as cancerous tissue, to be removed from the body, and lights to illuminate the surgical site.

Each instrument has a unique control interface for its operation, so a surgeon, or pair of surgeons, must independently operate each device. For example, a surgeon might use a first foot pedal to control an electrocautery device, a second foot pedal to operate a robotic arm, and another interface to operate a laser. The handles and a screen are typically integrated into a console operated by the surgeon to control the various robotic arms and medical instruments.

It typically requires a certain amount of time to train surgeons to use these robotic systems. Training has historically involved human cadavers. More recently, a company called Kindheart has adapted organs derived from dead animals, including heart, lungs, and the like, with tubing, pumps, switches, and the like, to mimic the action of living organs. For example, a heart can pump with heartbeats set to motion by a pump so that the heart rate is adjustable and controllable, and lungs can inflate and deflate on command.

There are some limitations associated with using these organs. One limitation is that, when theater blood is pumped through the organs, detergents commonly found in theater blood can cause the blood to foam.

Another limitation is that the osmolarity of theater blood is typically not the same as regular blood. As a result, organs can swell as they uptake fluid which is at a lower osmolality than regular blood. For example, a pig heart can suffer from pulmonary edema when the blood composition is too "watery."

A third limitation is that the components of theater blood do not allow the blood to clot. There are various clotting agents which a surgeon can use to induce blood clots, including various plant starches, and various biological factors. For example, there are various proteins in the blood that are essential for blood to coagulate.

Biological clotting factors circulate in the blood as inert proteins until a cascade of events initiates their conversion into active components which participate in blood clotting. Clotting factors interact with each other and other enzymes in the blood, such as fibrin and thrombin, to form blood clots. Various clotting factors include clotting factor I (fibrinogen), clotting factor II (prothrombin), clotting factor V (proaccelerin), clotting factor VII (cothromboplastin), clotting factor IX (plasma thromboplastin), and clotting factor X (Stuart-Prower factor).

Other clotting agents work by dehydrating the wound, and, optionally, crosslinking the proteins in blood to form a clot. For more traumatic wounds, such as bullet wounds and the like, there are products such as WoundSeal Powder, which includes a hydrophilic polymer and potassium ferrate. When the powder is poured onto a bleeding wound, the hydrophilic polymer instantly dehydrates the blood by absorbing only the plasma or liquid portion of the blood, and the potassium ferrate dissolves, releasing iron that agglomerates (binds together) the blood proteins and other solids to create an occlusive seal.

Other hemostatic agents include chitosan, such as the chitosan-based Celox product, and corn or potato starch, such as the biopolymeric, microporous potato starch particles in TraumaDEX. Chitosan is a positively-charged material, and functions by attracting negatively-charged red blood cells.

These wound-sealing agents do not necessarily replace traditional surgical closure techniques like suturing, clipping or stapling. However, they can improve the surgical technique, for example, by securing sutures against fluid loss, closing air leaks during lung re-sectioning procedures, or improving hemostasis (e.g. oozing in organ tissues, vascular graft operations, or endoscopic treatment of bleeding gastroduodenal ulcers).

These clotting factors are often used in abdominal surgery (e.g. after rupture or resection of liver, spleen or pancreas), cardiovascular surgery (e.g. during bypass surgery), orthopedic surgery (e.g. after bone marrow removal particularly in patients with bleeding tendency), thoracic surgery (e.g. to seal pulmonary fistulae), neurology (e.g. during plastic surgery of durae or dural repair), and urology (e.g. after resection of renal tumors). Accordingly, it would be useful to have a fake blood composition, for use in a simulated surgical setting, which would clot in a similar manner to real blood, and allow surgeons to practice using these clotting factors.

The present invention provides artificial, or fake, blood compositions which address one or more of these limitations.

SUMMARY OF THE INVENTION

In one embodiment, the invention relates to an artificial (fake) blood composition for use in simulated surgical procedures. The composition is not intended for use in replacing blood in actual living animals or humans. However, it includes components which allow it to be used as a simulated blood for simulated surgical procedures, and, in some embodiments, to physically clot when exposed to a clotting agent.

The fake blood composition includes one or more colorants, including dyes and inks, which preferably color the composition red, but which can be any desired color. Examples of such colorants include, but are not limited to, food dyes such as red dye #40 and FD&C blue #1. Although red dyes can be used exclusively, blue or green dyes can be used to achieve a more realistic shade. As a general rule, arterial blood is bright red, while venous blood is a dark maroon color.

The composition further includes a protein, which can be a milk protein such as whey (including whey isolate and whey concentrate) or casein, egg white protein, an animal protein, such as beef protein, a vegetable protein, such as soy, pea, rice, or hemp, or combinations thereof.

The composition can optionally include sugars, such as glucose, fructose, corn syrup, and the like, and thickeners, such as xanthan gum and vegetable starches, such as potato starch, corn starch and hydroxyethyl starch (HES). However, if used, thickeners should be present in an amount sufficient that the blood has a viscosity within a range of plus or minus about 20 percent the viscosity of human blood.

The fake blood composition can optionally include one or more salts, including sodium and potassium chloride, and buffers such as those including phosphate, ascorbate, acetate, and similar salts, and their conjugate acids. For example, standard 0.9% phosphate buffered saline can be used.

The amount of salts, sugars, and proteins should be selected to provide a fake blood composition with sufficient protein content to enable the blood to be clotted when clotting agents such as potato starch, corn starch, and hydroxyethyl starch are used, and with an osmolality and osmolarity within about 20% of that of human blood. Blood osmolality is typically measured in milliosmoles per kilogram, and a normal result is typically between about 275 and about 303 milliosmoles per kilogram. Accordingly, the fake blood described herein preferably has an osmolality between about 220 and about 400 milliosmoles per kilogram.

The pH of the fake blood composition is preferably within one pH unit of the normal blood pH, which is around a pH of 7.4.

In some embodiments, it can be desirable to include a detergent, such as a cationic, anionic, non-ionic, or zwitterionic surfactant, in an amount suitable to allow the fake blood to be more easily removed from clothing than if the detergent is not present. However, in those embodiments where the composition includes a detergent, it is also preferable to include a suitable defoamer. Otherwise, as the blood composition is pumped through organs in a simulated surgical procedure, the blood can foam undesirably.

Preservatives can also be present, in an amount sufficient to extend the useful shelf life of the composition.

In one embodiment, the compositions are liquid solutions or dispersions. Because of the protein content, the compositions can quickly degrade if not stored in an aseptic manner. The compositions can be cold filtered (a process known as microfiltration, or MF), for example, through a filter of a suitable size (for example, around a 0.2 micron or 0.5 micron filter) to filter out bacteria, and/or can be pasteurized. MF membranes have been used in the dairy industry, particularly for milk and whey processing, to remove bacteria and the associated spores from milk. The milk can then be stored, or can be subjected to pasteurization to allow for an extended shelf-life. If pasteurization is performed, care should be taken to avoid denaturing the proteins.

In another embodiment, the components of the fake blood are present in powder form, for later reconstitution. The fake blood can be reconstituted before use.

In use, the blood can be passed through the arteries and/or veins of human organs, animal organs, or synthetic organs during simulated surgical procedures. If desired, a clotting agent, such as potato starch, corn starch, hydroxyethyl starch, or chitosan, can be applied to any leaks, such as inadvertent nicks, suture lines, staple lines, and the like.

In another embodiment, a cadaver, human organs, animal organs, or synthetic organs can be filled with the blood composition, or, alternatively, with human or animal blood, and pre-cut in pre-selected areas. The cuts are then sealed with a clotting agent, such as corn starch, potato starch, or hydroxyethyl starch.

To simulate a "bleeder," the blood composition can include an agent which dissolves the clot, such as an amylase, or an amylase or other clot-dissolving agent can be added during the simulated surgery without the physician's knowledge, for example, via an IV line, and as the clot dissolves, the organ will "bleed." The surgeon can then practice how to deal with an emergency bleed, whether by removing the robotic instruments and going in manually, or by using a laser, additional clotting agent, mechanical means such as sutures and/or staples, and the like.

Where these types of pre-treated organs are used, they can be supplied in kit form, where the organ is supplied with the artificial blood described herein, along with an agent which dissolves the clot, such as an amylase or protease enzyme, or the blood itself can include an amylase enzyme.

The time during which the amylase enzyme dissolves the clot will depend on a number of factors, including the pH and temperature of the artificial blood, the thickness of the clot, the concentration of the enzyme, and the like. Those of skill in the art can readily adjust these factors to arrive at a suitable time frame for a clot to dissolve.

The blood can be supplied, for example, in IV bags or other suitable containers. The bags or containers can be attached to suitable tubing, which can be attached to suitable pumps and/or valves, which can be used to pass the blood through the cadaver, the human organs, the animal organs, or the synthetic organs.

The organs and blood described herein can be part of a robotic simulated surgical system.

Aspects of the teachings contained within this disclosure are addressed in the claims submitted with this application upon filing. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

Other systems, methods, features and advantages of the disclosed teachings will be or will become apparent to one with skill in the art upon examination of the following figures and detailed description. It is intended that all such additional systems, methods, features and advantages be included within the scope of and be protected by the accompanying claims.

DETAILED DESCRIPTION

In the following detailed description, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

In one embodiment, the invention described herein relates to artificial blood compositions for use in simulated surgical procedures. The compositions include a component, such as protein or urea, which can be clotted using conventional clotting agents, such as corn starch, potato starch, hydroxyethyl starch ("HES"), chitosan, and the like. The compositions can be in liquid form, or can be in the form of a reconstitutable powder.

In another embodiment, the invention relates to isolated tissue, organs, or organ blocks, which can be from cadavers, animals, or synthetic sources, where the tissue, organs, or organ blocks have been modified to include a clot, which clot can be unclotted using either the blood composition or an extraneous compound, so as to simulate a "bleeder" during a simulated surgical procedure.

In another embodiment, the invention described herein relates to kits for use in simulated surgical procedures, where the kits include the artificial blood compositions and isolated tissue, organs, organ blocks, which can be from cadavers, animals, or synthetic sources. In one aspect of this embodiment, the tissue, organs, or organ blocks include a clot, formed by cutting the tissue, organs, or organ blocks, and forming a clot using either blood or the blood composition described herein, and a clotting agent. The kits can further include an anti-clotting agent, such as an amylase or protease, to dissolve the clot and start the flow of blood through the cut.

The individual components of the compositions and kits are described in more detail below.

I. Artificial Blood Compositions

Dyes/Colorants

The fake blood composition includes one or more colorants, including dyes and inks, which preferably color the composition red, but which can be any desired color. Examples of such colorants include, but are not limited to, food dyes such as red dye #40 and FD&C blue #1. Although red dyes can be used exclusively, blue or green dyes can be used to achieve a more realistic shade. As a general rule, arterial blood is bright red, while venous blood is a dark maroon color.

Representative dyes that can be used include Citrus Red No. 2, FD&C Red No. 3, FD&C Red No. 40, FD&C Red No. 3, FD&C Red No. 4, D&C Red No. 6, D&C Red No. 7, D&C Red No. 17, D&C Red No. 21, D&C Red No. 22, D&C Red No. 27, D&C Red No. 28, Red No. 30, D&C Red No. 31, D&C Red No. 33, D&C Red No. 34, D&C Red No. 36, D&C Red No. 39, FD&C Red No. 40, FD&C Blue No. 1, D&C Blue No. 4, D&C Blue No. 6, D&C Blue No. 9, FD&C Green No. 3, D&C Green No. 5, D&C Green No. 6, D&C Green No. 8, and Cochineal extract.

Proteins

The compositions further include a protein, which can be a milk protein such as whey (including whey isolate and whey concentrate) or casein, egg white protein, an animal protein, such as beef protein, a vegetable protein, such as soy, pea, rice, or hemp, or combinations thereof.

Isolated proteins can be preferred, as they can impart the least "haze" to the blood, and result in a more natural appearance. However, if haze is not of concern, non-isolated proteins, such as milk products, including low-fat and non-fat milk, can be used.

Any suitable protein can be used, so long as it can be "clotted" upon exposure to solutions of clotting agents, as such are defined herein.

The concentration of the protein can vary, but is typically within the range of between about 0.1 and 10 by weight of the blood composition (dry weight).

Sugars/Thickeners/Salts

Although not necessary, the compositions can include one or more sugars. Examples of sugars include glucose, dextrose, fructose, corn syrup, and the like. The concentration of the sugar can vary, but is typically within the range of between about 0.1 and 2 by weight of the blood composition (dry weight).

The compositions can also include thickeners, such as xanthan gum and vegetable starches, such as potato starch, corn starch and hydroxyethyl starch (HES). At some concentration, these thickeners will cause the blood to thicken to the extent that it mimics a blood clot. However, if used at low enough concentrations, thickeners can be present in an amount sufficient that the blood has a viscosity within a range of plus or minus about 20 percent the viscosity of human blood.

The compositions can optionally include one or more salts, including sodium and potassium chloride, and buffers such as those including phosphate, ascorbate, acetate, and similar salts, and their conjugate acids. For example, standard 0.9% phosphate buffered saline can be used.

The amount of salts, sugars, and proteins should be selected to provide a fake blood composition with sufficient protein content to enable the blood to be clotted when clotting agents such as potato starch, corn starch, and hydroxyethyl starch are used, and with an osmolality and osmolarity within about 20% of that of human blood. Blood osmolality is typically measured in milliosmoles per kilogram, and a normal result is typically between about 275 and about 303 milliosmoles per kilogram. Accordingly, the fake blood described herein preferably has an osmolality between about 220 and about 400 milliosmoles per kilogram.

In one embodiment, the ion concentration is selected to approximate that in 0.9% phosphate buffered saline, that is, to be within around 20% plus or minus of this ion concentration, so as to provide a fake blood composition that can conduct electricity. This can be particularly important where a surgeon practicing a simulated surgical procedure intends to use electro-cautery to seal a wound. A fake blood composition without a sufficient ion concentration would not conduct electricity in an efficient enough manner to simulate the actual electro-cautery conditions a surgeon would expect from a live patient, thus providing the surgeon with a less realistic training scenario.

Where electro-cautery is to be practiced, it is also important to provide a source of "ground." In one embodiment, this can be accomplished by attaching a wire directly to one of the tissues, organs, or organ systems described herein, for example, using an alligator clip. In one aspect of this embodiment, the clip can be attached to the esophagus, assuming the organ or organ system has an esophagus. The "ground" is sufficiently far from the area in which the electro-cautery is to take place that it can avoid significant complications, although the organ may tend to burn at or near where the clip is located.

In another embodiment, where the tissues, organs, or organ systems described herein reside on a conductive tray, such as a metal tray, a piece of conductive tape can be adhered to the tray. An alligator clip, adhesive pad, or other connective device attached to the wire can then be adhered to the conductive tape. Examples of conductive tapes include, but are not limited to, stainless steel tape, copper tape, silver tape, aluminum tape, and carbon fiber tape.

The pH of the compositions is preferably within one pH unit of the normal blood pH, which is around a pH of 7.4.

Detergents

In some embodiments, it can be desirable to include a detergent, such as a cationic, anionic, non-ionic, or zwitterionic surfactant, in an amount suitable to allow the fake blood to be more easily removed from clothing than if the detergent is not present.

Suitable nonionic surfactants include any of the conventional nonionic surfactant types typically used in liquid detergent products. These include alkoxylated fatty primary alcohol-based or secondary alcohol-based surfactants and amine oxide surfactants. In one aspect, for use in the liquid detergent products herein are those nonionic surfactants which are normally liquid.

Suitable nonionic surfactants for use herein include the alcohol alkoxylate nonionic surfactants. Alcohol alkoxylates are materials which correspond to the general formula: $R^1(C_mH_{2m}O)_nOH$ wherein $R^1$ is a $C_{8-16}$ alkyl group, m is from 2 to 4, and n ranges from about 2 to 12. In one aspect, $R^1$ is an alkyl group, which may be primary or secondary, that comprises from about 9 to 15 carbon atoms, or from about 10 to 14 carbon atoms. In one aspect, the alkoxylated fatty alcohols will also be ethoxylated materials that contain from about 2 to 12 ethylene oxide moieties per molecule, or from about 3 to 10 ethylene oxide moieties per molecule.

The alkoxylated fatty alcohol materials will frequently have a hydrophilic-lipophilic balance (HLB) which ranges from about 3 to 17 from about 6 to 15, or from about 8 to 15. Alkoxylated fatty alcohol nonionic surfactants include those marketed under the tradenames Neodol and Dobanol by the Shell Chemical Company.

Suitable non-ionic surfactants can also include ethoxylated nonionic surfactants, which may include primary and secondary alcohol ethoxylates, especially the $C_{8-20}$ aliphatic alcohols ethoxylated with an average of from 1 to 50 or even 20 moles of ethylene oxide per mole of alcohol, and more especially the $C_{10-15}$ primary and secondary aliphatic alcohols ethoxylated with an average of from 1 to 10 moles of ethylene oxide per mole of alcohol. Non-ethoxylated alcohol nonionic surfactants include alkylpolyglycosides, glycerol monoethers, and polyhydroxyamides (glucamide), glycereth cocoate or mixtures thereof.

The ethoxylated alcohol non-ionic surfactant can be, for example, a condensation product of from 3 to 8 mol of ethylene oxide with 1 mol of a primary alcohol having from 9 to 15 carbon atoms.

The non-ionic surfactant can include a fatty alcohol ethoxylate of formula $R(EO)_n$, wherein R represents an alkyl chain between 4 and 30 carbon atoms, (EO) represents one unit of ethylene oxide monomer and n has an average value between 0.5 and 20.

Another suitable type of nonionic surfactant useful herein comprises the amine oxide surfactants. Amine oxides are materials which are often referred to in the art as "semi-polar" nonionics. Amine oxides have the formula: $R(EO)_x(PO)_y(BO)_zN(O)(CH_2R')_2 \cdot qH_2O$. In this formula, R is a relatively long-chain hydrocarbyl moiety which can be saturated or unsaturated, linear or branched, and can contain from 8 to 20, 10 to 16 carbon atoms, or is a $C_{12-16}$ primary alkyl. R' is a short-chain moiety, in one aspect R' may be selected from hydrogen, methyl and $—CH_2OH$. When x+y+z is different from 0, EO is ethyleneoxy, PO is propyleneneoxy and BO is butyleneoxy. Amine oxide surfactants are illustrated by $C_{12-14}$ alkyldimethyl amine oxide.

Non-limiting examples of nonionic surfactants include: a) $C_{12-18}$ alkyl ethoxylates, such as, NEODOL® nonionic surfactants from Shell; b) $C_{6-12}$ alkyl phenol alkoxylates wherein the alkoxylate units are a mixture of ethyleneoxy and propyleneoxy units; c) $C_{12-18}$ alcohol and $C_{6-12}$ alkyl phenol condensates with ethylene oxide/propylene oxide block polymers such as Pluronic® from BASF; d) $C_{14-22}$ mid-chain branched alcohols, BA, as discussed in U.S. Pat. No. 6,150,322; e) $C_{14}$-$C_{22}$ mid-chain branched alkyl alkoxylates, $BAE_x$, wherein x if from 1-30, as discussed in U.S. Pat. Nos. 6,153,577, 6,020,303 and 6,093,856; f) Alkylpolysaccharides as discussed in U.S. Pat. No. 4,565,647 to Llenado, issued Jan. 26, 1986; specifically alkylpolyglycosides as discussed in U.S. Pat. Nos. 4,483,780 and 4,483,779; g) Polyhydroxy fatty acid amides as discussed in U.S. Pat. No. 5,332,528, WO 92/06162, WO 93/19146, WO 93/19038, and WO 94/09099; and h) ether capped poly(oxyalkylated) alcohol surfactants as discussed in U.S. Pat. No. 6,482,994 and WO 01/42408.

Representative anionic surfactants include linear alkyl benzene sulfonate, alkyl ethoxylate sulphate and combinations thereof. Suitable anionic surfactants include any of the conventional anionic surfactant types typically used in liquid detergent products. These include the alkyl benzene sulfonic acids and their salts as well as alkoxylated or non-alkoxylated alkyl sulfate materials.

Exemplary anionic surfactants are the alkali metal salts of $C_{10-16}$ alkyl benzene sulfonic acids, or $C_{11-14}$ alkyl benzene sulfonic acids. In one aspect, the alkyl group is linear and such linear alkyl benzene sulfonates are known as "LAS". Alkyl benzene sulfonates, and particularly LAS, are well known in the art. Such surfactants and their preparation are described for example in U.S. Pat. Nos. 2,220,099 and 2,477,383. Especially useful are the sodium, potassium and amine linear straight chain alkylbenzene sulfonates in which the average number of carbon atoms in the alkyl group is from about 11 to 14. Sodium $C_{11-14}$, e.g., $C_{12}$, LAS is a specific example of such surfactants.

Specific, non-limiting examples of anionic surfactants useful herein include the acid or salt forms of: a) $C_{11-18}$ alkyl benzene sulfonates (LAS); b) $C_{10-20}$ primary, branched-chain and random alkyl sulfates (AS), including predominantly $C_{12}$ alkyl sulfates; c) $C_{10-18}$ secondary (2,3) alkyl sulfates with non-limiting examples of suitable cations including sodium, potassium, ammonium, amine and mixtures thereof; d) $C_{10-18}$ alkyl alkoxy sulfates ($AE_xS$) wherein x is from 1-30; e) $C_{10-18}$ alkyl alkoxy carboxylates in one aspect, comprising 1-5 ethoxy units; f) mid-chain branched alkyl sulfates as discussed in U.S. Pat. Nos. 6,020,303 and 6,060,443; g) mid-chain branched alkyl alkoxy sulfates as discussed in U.S. Pat. Nos. 6,008,181 and 6,020,303; h) modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548; i) methyl ester sulfonate (MES); and j) alpha-olefin sulfonate (AOS).

A suitable anionic detersive surfactant is predominantly alkyl $C_{16}$ alkyl mid-chain branched sulphate. A suitable feedstock for predominantly alkyl $C_{16}$ alkyl mid-chain branched sulphate is beta-farnesene, such as BioFene™ supplied by Amyris, Emeryville, Calif.

The amount of detergent is typically less than around 1% by weight of the composition (dry weight), but the amount can be adjusted as desired.

Defoamers

In those embodiments where the composition includes a detergent, it is also preferable to include a suitable defoamer. Otherwise, as the blood composition is pumped through organs in a simulated surgical procedure, the blood can foam undesirably.

Representative defoamers include, but are not limited to, hydrophobic silicas, for example silicon dioxide or fumed silica in fine particle sizes, including Foam Blast® defoamers available from Emerald Performance Materials, including Foam Blast® 327, Foam Blast® UVD, Foam Blast® 163, Foam Blast® 269, Foam Blast® 338, Foam Blast® 290, Foam Blast® 332, Foam Blast® 349, Foam Blast® 550 and Foam Blast® 339, which are proprietary, non-mineral oil defoamers. In embodiments, defoamers can be used in an amount of 0.5 phr, or less, for example, 0.05 phr, 0.04 phr, 0.03 phr, 0.02 phr, or 0.01 phr.

Defoamers also include siloxane-based polymers, including organomodified siloxane polymers. The organomodified siloxane polymers may comprise aryl or alkylaryl substituents optionally combined with silicone resin and/or modified silica. In one embodiment, the defoamer is selected from organomodified silicone polymers with aryl or alkylaryl substituents combined with silicone resin and optionally a primary filler. Particularly preferred are compounds consisting of organomodified silicone polymers with aryl or alkyaryl substituents combined with silicone resin and modified silica as described in U.S. Pat. Nos. 6,521,586 B1, 6,521,587 B1, US Patent Applications 2005 0239908 A1, 2007 01673 A1 to Dow Corning Corp. and US Patent Application 2008 0021152 A1 to Wacker Chemie AG.

The defoamers are typically present in a concentration of between around 0.01 and 2 by weight of the composition (dry weight).

Preservatives/Antioxidants

Preservatives and/or antioxidants can also be present, in an amount sufficient to extend the useful shelf life of the composition.

Representative preservatives include Quaternium-15 (a bactericidal and fungicidal preservative), Polyquaternium-10, and Methylisothiazolinone, or MIT, a biocide and preservative.

Representative antioxidants include amino acids (e.g. glycine, histidine, tyrosine, tryptophan) and their derivatives, imidazole (e.g. urocanic acid) and derivatives, peptides such as D,L-carnosine, D-carnosine, L-carnosine and derivatives (e.g. anserine), carotenoids, carotenes (e.g. alpha-carotene, beta-carotene, lycopene) and derivatives, chlorogenic acid and derivatives, lipoic acid and derivatives (e.g. dihydrolipoic acid), aurothioglucose, propylthiouracil and other thiols (e.g. thioredoxin, glutathione, cysteine, 14inoleic, cystamine and its glycosyl-, N-acetyl-, methyl-, ethyl-, propyl-, amyl-, butyl- and lauryl-, palmitoyl-; oleyl-, y-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinesulfoximine, buthioninsulfone, penta-, hexa-, heptathioninsulfoximine) in very low compatible doses (e.g. pmol bis .mu.mol/kg), additionally (metal)-chelators (such as alpha-hydroxyfatty acids, palmic-, phytinic acid, lactoferrin), beta-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as .gamma.-linoleic acid, 15inoleic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, ascorbyl-acetate), tocopherol and derivates (such as vitamin-E-acetate), mixtures of nat. vitamin E, vitamin A and derivatives (vitamin-A-palmitate and -acetate) as well as coniferylbenzoate, rutinic acid and derivatives, alpha-glycosylrutin, ferulic acid, furfurylideneglucitol, carnosine, butylhydroxytoluene, butylhydroxyanisole, trihydroxybutyrophenone, urea and its derivatives, mannose and derivatives, zinc and derivatives (e.g. ZnO, $ZnSO_4$), selen and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount of at least 0.01 wt. % of the total weight of the composition. Preferably about 0.01 wt. % to about 10 wt. % of the total weight of the composition of the present invention is present. Most preferred, one or more preservatives/antioxidants are present in an amount about 0.1 wt. % to about 1 wt. %.

Isotonic/Iso-Osmolar Solutions

It is important that the blood formulations be within 20% of the osmolality of normal blood. Solutions/dispersions which have substantially the same osmolality of blood are isotonic. Solutions/dispersions which contain fewer particles and exert a lower osmotic pressure than 0.9% saline are called hypotonic, and those exerting higher osmotic pressures are referred to as hypertonic. The "clinical" significance of all this is to insure that isotonic or iso-osmolar solutions do not damage the animal or human tissue in the organs used in the simulated surgical systems.

The pH of the compositions is preferably within one pH unit of the normal blood pH, which is around a pH of 7.4.

Those of skill in the art can readily determine what the concentration of the various components should be to provide a desirable color, viscosity, and clotting ability to approximate actual blood in simulated surgical procedures, using the teachings provided herein.

II. Methods of Making the Artificial Blood Compositions

In one embodiment, the compositions are supplied in liquid form. Due to the protein/urea content, the compositions should be packaged in an aseptic manner, or there is a risk of bacterial contamination.

To form the compositions, the various components are mixed in a desired ratio. The osmolality and/or pH of the compositions can optionally be measured, to ensure quality control. The compositions are preferably treated to remove bacteria and other microorganisms. Bacteria and other microorganisms, though not viruses, can be removed by filtration.

To remove bacteria and other microorganisms by filtration, the solution/dispersion is typically passed through a porous surface as a result of a vacuum created on the other side of that surface, or as a result of pressure exerted on the liquid being filtered.

There are a number of types of bacterial filters which can be used. For example, glass filters are round discs consisting of porous glass, sealed into funnels. Ceramic filters are made of kaolin or kieselguhr; and the Chamberland and Berkefeld filters belong to this group. The former are shaped like hollow cylinders with a sealed base and are equipped with a glazed neck on top to which a rubber tube is attached to draw the fluid through the wall of the filter. Membranous filters, for example, those produced from acetylcellulose, nitrocellulose, and cellulose esters, can also be used.

The pore size is varied in different bacterial filters, and typically are less than about 0.75 microns, preferably less than about 0.5 microns, and more preferably, less than about 0.2 microns. In addition to the pore dimension and the created vacuum (or pressure), several other factors—for example, electrical charge, viscosity and reaction of the fluid being filtered, and adsorption phenomena—can influence the speed of filtration.

Bacterial filters can be used to sterilize liquids for which it is desirable to avoid heat pasteurization. Since the compositions described herein include proteins, which can be denatured if exposed to too much heat, it may be desirable to avoid heat pasteurization. That said, milk products have been pasteurized without overly denaturing the milk proteins, so it is also possible to heat pasteurize the compositions, alone or in combination with bacterial filtration.

After the filtration step, the resulting liquid can then be packaged. Once packaged, the liquid can be subjected to heat sterilization (pasteurization). The degree of sterilization is based on the time that the product is subjected to specific temperatures, and is a culmination of all thermal treatments that the product encounters during processing. Consequently, a desired sterilization value may be achieved through a variety of processing conditions. Overly high temperatures or excessively long exposures to elevated temperatures, can adversely affect the long term stability of the compositions, for example, by inducing gelation or browning. However, if the compositions are to be used within a short time frame after they are packaged, this may not present a problem.

In another embodiment, the blood compositions are provided as dry compositions, which upon addition of an adequate amount of an aqueous medium form a solution or dispersion suitable for use in simulated surgical procedures. The solution or dispersion forms spontaneously upon addition of the liquid component, i.e. little or no mechanical mixing is required.

The dry compositions can be prepared by either providing the components in a powder form, or preparing a solution/dispersion of the components, and drying the solution/dispersion. The drying step can be carried out by freeze drying (lyophilization), spray drying, drum drying, and the like.

The clotting agents described herein can be provided as a solution, dispersion, paste, spray, powder, and the like. Several clotting agents are commercially available, and can be included in the kit in their commercial form.

Similarly, the clot dissolving agents described herein can be provided as a solution, dispersion, paste, spray, powder, and the like. In use, they are either added to the blood compositions, or introduced via injection into an IV bag.

III. Clotting Agents and Anti-Clotting Agents

Representative blood clotting agents commonly used in surgical procedures include, but are not limited to, a starch, alginate, chitosan, a hydrophilic polyamine, a chitosan derivative, polylysine, polyethylene imine, xanthan, carrageenan, quaternary ammonium polymer, chondroitin sulfate, a modified cellulosic polymer, a dextran, hyaluronan or combinations thereof. Commercially-available clotting agents include the chitosan-based Celox product, and the biopolymeric, microporous potato starch particles in TraumaDEX.

Representative starches include potato starch, corn starch, and hydroxyethyl starch. The clotting agents can be present in the form of a powder, or a liquid, and can be applied during surgery, for example, by spraying them onto a wound, applying them to the wound as a liquid or powder, and other application methods known to those of skill in the art.

To dissolve the clots, an anti-clotting agent is used. Where the clotting agent is a starch, an amylase can be used. Examples of amylases include bacterial amylase solution, at a concentration, for example, of 3000 SKB units/ml, a fungal amylase powder, for example, at 40,000 SKB units/g, an amyloglucosidase solution, for example, at around 75 AG units/ml, and human salivary amylase ("ptyalin"). Commercially-available amylases include, for example, α-amylase from *Aspergillus oryzae* (Sigma-Aldrich, St. Louis, Mo., Catalog #10065), α-amylase from *Bacillus subtilis* (Sigma, catalog #10070), α-amylase from human saliva (Sigma, catalog #A1031), and β-amylase from sweet potato (Sigma, catalog #A7005). Pancreatin includes amylase, lipase, and protease. Where the clotting agent is chitin, a chitinase enzyme can be used. Representative chitinases include EC 3.2.1.14, chitodextrinase, 1,4-beta-poly-N-acetylglucosaminidase, poly-beta-glucosaminidase, beta-1,4-poly-N-acetyl glucosamidinase, poly [1,4-(N-acetyl-beta-D-glucosaminide)] glycanohydrolase, (1→4)-2-acetamido-2-deoxy-beta-D-glucan glycanohydrolase). These hydrolytic enzymes break down glycosidic bonds in chitin.

Where a polycationic polymer is used as a clotting agent, such as polyethylene imine, a polyanionic polymer, such as polyanionic cellulose, can be used to disrupt the binding of the cationic polymer with the proteins in the blood compositions, by forming stronger bonds with the polycationic polymer.

IV. Vasodilators

When animal tissue, organs and organ blocks are preserved and stored, they are typically stored using refrigeration, at temperatures cold enough to cause vasoconstriction.

It is advantageous to reverse the vasoconstriction to allow the blood compositions to flow/perfuse to the edge of the tissue, organs, or organ blocks. Typically, if the animal tissue, organs or organ blocks are warmed to body temperature, the vasoconstriction is reversed, but the tissue, organs and organ blocks can quickly become susceptible to rotting, and the associated odor can be unpleasant for the surgeon carrying out the simulated surgical procedures.

For this reason, it can be advantageous to include a vasodilator in the blood compositions described herein. The vasodilator can offset the vasoconstriction caused by the cold temperatures, while still allowing the tissue, organs, or organ blocks to be maintained at a cold temperature. This has the effect of minimizing degradation of the tissue, organs, or organ blocks, while also allowing the blood compositions to perfuse throughout the tissue, organs, or organ blocks.

Representative vasodilators which can be present in the blood compositions described herein include nitroglycerin, ephedrine, niacin, nicotinamide, nicotinic acid, diltiazem, papaverine, adenosine, Caverject (alprostadil), Adempas (riociguat), Apresoline (hydralazine), Loniten (minoxidil), Natrecor (nesiritide), Nitropress (nitroprusside), nitrates, flavonoids, magnesium salts, and L-arginine. Among these, nitroglycerine, papaverine, and adenosine can be preferred, with nitroglycerine being most preferred.

The vasodilators are present in a concentration effective to reverse or partially reverse the vasoconstriction resulting from cold storage of the tissue, organs, or organ blocks. Those of skill in the art can readily determine an appropriate concentration, based at least in part on the dosages of these agents when used to bring about vasodilation in living human patients.

V. Use of the Artificial Blood in Simulated Surgical Procedures

The artificial blood compositions described herein can be used in simulated surgical procedures, including, but not limited, to those performed using robotics. Examples of simulated surgical procedures include heart by-pass operations, valve replacements or repair, lung re-sectioning, tumor removal, prostatectomy, appendectomy, hernia operations, stomach stapling/lap band operations, orthopedic surgery, such as rotator cuff repair and arthroscopic knee surgery. In addition to actual operations, specific skill sets can be developed, for example, vein dissection, use of staplers, cautery, and the like.

During the surgery, the protein or urea in the blood compositions allows the blood to be "clotted" using blood clotting agents.

Each of these surgeries and/or skill sets can be practiced using an appropriate tissue, organ or organ block, as discussed in detail below, where the artificial blood is passed through the tissue, organ, or organ block during surgery.

Typical simulated surgical systems include one or more surgical simulator units that include animal, cadaver, or artificial tissues, organs, or organ systems, providing a non-living but realistic platform on which to perform surgery. The systems can also include one or more instruments for performing robotic surgery, so that one or more simulated surgical procedures can be performed on tissues, organs, or organ systems in the surgical simulator units. The systems can optionally include a telecommunications system which allows remote access to, and control of, the instruments used to perform robotic surgery, thus allowing simulated robotic surgery to be performed remotely.

Types of Tissue/Organs

Simulated surgery involves performing an operation, whether in a traditional manner, or using robotics, on animal, cadaver human, or artificial tissue and/or organs, and/or organ blocks including the organs, or combinations thereof. These tissues, organs, and/or organ blocks are included in simulated surgical devices, such that a surgeon can perform lifelike surgery on real, or at least realistic, tissue.

One or more of these tissue, organs, and/or organ blocks can be hooked up to a source of the artificial blood compositions described herein to simulate bleeding, and/or can be hooked up to a source of a gas and/or vacuum, which can be used to simulate organ movement.

For example, animal lungs can be expanded and contracted to simulate normal breathing, or to simulate other types of breathing, such as shallow breathing, coughing, and the like. A heart can be expanded and contracted to simulate a heartbeat, for example, by inflating one or more balloons inside the heart, for example, inside the ventricles.

So as to allow connection to a source of a gas or vacuum (to inflate/deflate the lung or cause the heart to "beat"), or to the artificial blood compositions described herein, the organs can be equipped with quick-connect tubes. Using these quick-connect tubes, the organs or organ blocks can be quickly incorporated into a surgical simulator, and attached to a source of air and vacuum, such as a bellows, an ambu bag, and the like. Where the surgical simulator includes a heart, the heart can be expanded and contracted, for example, using a balloon attached to a source of air and a source of vacuum.

Though judicious application of a gas to a balloon or other expandable member, different heartbeat rhythms can be produced, simulating a normal heartbeat, a distressed heartbeat, arrhythmias, a heart attack, and the like. In one aspect of this embodiment, a surgeon can simulate the steps needed to be taken following a myocardial infarction, where the surgical instruments must often be removed before resuscitation efforts can be initiated.

A group of animal tissue collections may be made from a series of animals before butchering for food so that no animals are sacrificed beyond what would be butchered for food. By collecting a series of tissue collections by the same facility using the same procedure from the same herd of animals (same breed, same age, same food), there will be extensive similarities among the collected tissue samples.

As is understood by those of skill in art, some features vary even between identical twins such as the vascular pattern around the exterior of the heart so some features cannot be closely controlled. However, certain degrees of variability can be decreased by clustering tissue samples by gender of donor animal, nominal weight of donor animal, or some other property of the animal or classification made of the harvested tissue sample.

The organs used in the surgical simulators can be preselected so as to have various defects, such as tumors, valve defects, arterial blockages, and the like, or can be selected to be as close to identical as possible. In the former embodiment, a surgeon can demonstrate a particular type of operation where a particular defect is present, and in the latter embodiment, a surgical instructor can demonstrate a technique to multiple students, using organs that are closely matched, so that the results would be expected to be the same if the students perform the surgery correctly.

In general, the organs may be characterized using a wide variety of available metrics. These may include volume of ventricles, stiffness of the muscle tissue (restitution test), specific gravity, % fat, pressure testing, presence or absence of tumors, blockage or arteries, etc. The recorded metrics will be specific to the scenario being replicated. Ideally, the organs selected are as close to the size and weight of human organs.

Examples of classification of the tissue samples may include:
A) Some characterization of the amount of fatty material surrounding the tissue of interest.
B) Some characterization of the pliability/stiffness of the tissue.
C) Some characterization of the properties of the relevant blood vessels such as degree of occlusion.
D) One way to characterize an organ is the time it takes for a fluid to drip out from a container and into an organ. As the receiving volume of the organ will be relatively uniform (for organs of the same size) this may characterize the ability of fluids to flow through the structures in the organ and out.

Representative Xenographic Organ Preparation

Porcine organ blocks including the heart with pericardium, lungs, trachea, esophagus, and 8-12 inches of aorta can be obtained from a local supplier. There is no need to sacrifice animals to obtain these organs or organ blocks, as these can be harvested from an animal before butchering the animal for food products.

Organ preparation can begin with an incision of the pericardium on the right posterior side of the heart, so it can later be reattached with no noticeable holes when viewed from the left side. The superior vena cava, inferior vena cava, right pulmonary artery, and right pulmonary veins can then be divided with care taken to leave as much vessel length as possible. After the right lung is fully detached, the organs can be washed extensively to remove coagulated blood from the heart and vessels. All divided vessels, except for the main branch of the right pulmonary artery and right superior pulmonary vein, can be tied off, for example, using 0-silk.

As an example of quick-connect tubes, small diameter plastic tubes with Luer-Lok® connectors can then be placed into the divided right pulmonary artery and right superior pulmonary vein, and fixed in place, for example, using purse-string sutures. To create distention of the aorta, one can inject silicone caulking to the level of the ascending aorta.

After the silicone cures, the brachiocephalic trunk and left common carotid can be tied off, for example, using 0-silk.

The left main stem bronchus can be occluded, for example, by stapling the divided right main stem bronchus as well as the proximal trachea. The left hilum can remain unaltered, and all modifications to the heart can be hidden by the pericardium during the procedure.

Following preparation, the organs can be stored at a relatively low temperature, for example, 4 degrees Celsius, in an alcoholic solution, for example, 10% ethanol containing ½ teaspoon of red food coloring. In this manner, the organs typically remain fresh for at least 1 month. Use of higher concentrations of alcohol, such as 40% ethanol, can preserve the organs for over a year, and, ideally, up to 18 months, and can perform as well as freshly-harvested organs.

Simulating "Bleeders"

While there is value in having intact organs on which to operate, there is also value in having organs with a defect such that, during surgery, the simulation can test the surgeon's ability to handle a "bleeder."

One of the benefits of the present invention is the ability to precisely create trauma in ex vivo tissue samples, for example, by making one or more incisions, then "clotting" the blood composition to close the incision. During surgery, the clot can be dissolved, for example, by appropriately placing an agent in the blood that dissolves the clot, or by injecting an agent that dissolves the clot into an IV. The clotting agents and clot dissolving agents include those described above.

Mimicking Blood Flow, Air Flow, and Heart Beats

Lightly pressurized artificial blood compositions can be provided through a connection, such as a quick connect fitting, to the umbilical cable port to provide the blood compositions into the divided right pulmonary artery and divided right superior pulmonary vein to distend and pressurize the venous and arterial systems. Static fluid pressure within the vessels can be achieved using gravity flow from an IV bag. Pressure is ideally limited, to avoid severe pulmonary edema. Extended perfusion times (1-2 hours) can be maintained without substantial fluid leakage into the airways by preparing the porcine organ block to occlude the left mainstem bronchus to inhibit leaking and loss of pressure.

As used in this specification, a quick connect fitting is one that may be connected to a corresponding fitting without using tools. A quick connect fitting can be used to connect to hydraulic line, pneumatic line, electrical line, and/or digital communication bus.

A balloon can be placed in the heart and connected to a closed system air source to allow for emulating the beating of a heart (such as at a rate of 78 beats per minute) to add to the sense of realism of the simulated surgical procedure.

Where an organ block includes lungs, the lungs can be inflated and deflated using the methods described herein. Inflation and deflation of lungs of a real patient causes the rise and fall of the mediastinum. To simulate this, an appropriate volume of air or some other fluid can be used to inflate and deflate an appropriately sized and placed container hidden under the tissue to be animated with movement. For example a respiration rate of 20 breaths per minute can be simulated by periodically expanding an air bladder, such as a whoopee cushion or an empty one-liter IV bag that is folded in half.

Rather than merely animating the tissue by causing it to rise and fall, one can connect lungs to a source of gas, such as air or nitrogen, and cycle the air going into and out of the lungs in such a way as to mimic respiration. For example, a bellows or an "Ambu bag," can be used to provide a "pulsatile" air supply. A suitable arrangement is described, for example, in U.S. Publication No. 2013/0330700.

In this manner, the organs and/or organ blocks can be animated by providing one quick connect fitting to connect the heart balloon to an air supply to provide a beating heart effect, and a second quick connect fitting can be connected to a different pneumatic connection to provide air to the lungs, providing lung movement to simulate breathing. A fluid quick connect fitting connected to the joined blood vessels can allow for slightly pressured simulated blood to be provided. One or more of these connections can be made to an umbilical cable.

As used in this specification, a quick connect fitting is one that may be connected to a corresponding fitting without using tools. A quick connect fitting can be used to connect to hydraulic line, pneumatic line, electrical line, and/or digital communication bus.

A master-controller can be used provide one or more fluids. The fluids may contain medical grade ethanol, dyes, and thickening agents. Medical grade ethanol has been found useful in maintaining the staged reality modules and in making the staged reality modules inhospitable to undesired organisms. Ethanol is useful compared to other chemicals which may be used to preserve tissue in that the ethanol maintains the pliability of the tissue so that it behaves like live tissue in a patient. A mixture with 40% ethanol works well, but the mixture should be made with an effort to avoid flammability when exposed to sparks or a cauterization process. Ethanol is desirable in that it does not produce a discernable odor to remind the participant that this is preserved tissue.

The master-controller may isolate the umbilical cable or cables from the fluid supply to allow the replacement of a module to allow the trainee to repeat a simulation with a new set of tissues, organs, or organ blocks.

Some simulated surgical settings can have a pre-prepared module made by connecting the venous and arterial systems together, so that one pressurized fluid supply can animate both the arterial and venous vessels by filling them with the blood compositions described herein. The pressure for the compositions can be maintained by mere fluid head as an IV bag is suspended at a desired height above the master-controller, or the master-controller may provide the compositions at a given pressure using conventional components.

The umbilical cable can be provided with two different blood compositions, one being dyed to resemble arterial blood and a second dyed to resemble venous blood.

The umbilical cable can also be provided with fluid lines for one or more non-blood fluids to be simulated such as digestive fluids, cerebral-spinal fluids, lymphatic fluids, fluids associated with pulmonary edema, pleural effusions, saliva, urine, or others fluids depending on the disease or trauma to be simulated.

The fluid and pneumatic connections used to connect the module to the various supplies on the umbilical cable can be any suitable connector for the desired pressure. Quick-connect fittings may be preferred, so that the act of replacing a module with a similar module to allow the trainee to try it again may be accomplished quickly.

Depending on the quick-connect fitting used, the port may need to have blanks inserted to close the port to flow. When a module is to be connected to the port, the blank is removed and the module is connected.

The master-controller can record the volume of fluids and gas provided to the particular lines or alternatively the pressure maintained on particular lines over time. This data record may be used to assess when a trainee effectively ligated a blood vessel or shut off some other structure such as a urinary tract.

Representative Endoscopic Surgical Simulator

Endoscopic procedures can be simulated, for example, using the Endoscopy VR Simulator from CAE Healthcare. This simulator is a virtual reality endoscopic simulation platform that uses realistic, procedure-based content to teach cognitive and motor skills training. It is an interactive system with tactile feedback that permits learning and practice without putting patients at risk. The tissue, while not animal tissue, looks real, and 'moves' when it is touched. The virtual patient exhibits involuntary muscle contractions, bleeding, vital sign changes, etc., and the surgeon feels feedback resistance during the simulated procedure.

Robotic Surgical Instruments

In the simulated surgical procedures described herein, one or more surgeons can perform surgery on the animal tissue, organs, and/or organ blocks using robotic surgical instruments. Typically, the robotic surgical devices include one or more arms, which control one or more tools, such as an endoscope (which provides the surgeon with the ability to see inside of the patient, and, typically, a tool selected from the group consisting of jaws, scissors, graspers, needle holders, micro-dissectors, staple appliers, tackers, suction irrigation tools, clip appliers, cutting blades, cautery probes, irrigators, catheters, suction orifices, lasers, and lights.

In robotically-assisted telesurgery, the surgeon typically operates a master controller to control the motion of surgical instruments at the surgical site from a location that may be remote from the surgical simulator (e.g., across the operating room, in a different room, or a completely different building from the surgical simulator).

The master controller usually includes one or more hand input devices, such as hand-held wrist gimbals, joysticks, exoskeletal gloves or the like. These control the movement of one or more of the robotic arms. Occasionally, line-of-sign/gaze tracking and oral commands are used to control movement of one or more of the robotic arms, and/or the audio/video components that transmit signal back to the surgeon.

For minimally invasive surgical procedures, the surgical instruments, controlled by the surgical manipulator, can be introduced into a simulated body cavity through a single surgical incision site, multiple closely spaced incision sites on the simulated body, and/or one or more natural orifices in the anatomy of the organ and/or organ block (such as through the rectum where a porcine or other animal gastrointestinal system is used as the organ block).

For some minimally invasive surgical procedures performed through particularly small entry ports, multiple surgical instruments may be introduced in a closely gathered cluster with nearly parallel instrument shafts.

A more detailed explanation of certain the components of robotic systems is provided below:

A robotic surgical system includes a master system, also referred to as a master or surgeon's console, for inputting a surgical procedure and a slave system, also referred to as a patient-side manipulator (PSM), for robotically moving surgical instruments at a surgical site within a patient. The robotic surgical system is used to perform minimally invasive robotic surgery. One example of a robotic surgical system architecture that can be used to implement the systems and techniques described in this disclosure is a da Vinci®. Surgical System manufactured by Intuitive Surgical, Inc. of Sunnyvale, Calif. Alternatively, a smaller scale robotic surgical system with a single manipulator arm may be suitable for some procedures. The robotic surgical system also includes an image capture system, which includes an image capture device, such as an endoscope, and related image processing hardware and software. The robotic surgical system also includes a control system that is operatively linked to sensors, motors, actuators, and other components of the master system and the slave system and to the image capture system.

The system is used by a system operator, generally a surgeon, who performs a minimally invasive simulated surgical procedure on a simulated patient. The system operator sees images, captured by the image capture system, presented for viewing at the master system. In response to the surgeon's input commands, the control system effects servo-mechanical movement of surgical instruments coupled to the robotic slave system.

The control system includes at least one processor and typically a plurality of processors for effecting control between the master system, the slave system, and the image capture system. The control system also includes software programming instructions to implement some or all of the methods described herein. The control system can include a number of data processing circuits (e.g., on the master system and/or on the slave system), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, control system may support wireless communication protocols such as Bluetooth, IrDA, HomeRF, IEEE 802.11, DECT, and Wireless Telemetry.

The robotic surgical system can also include an instrument chassis that couples to the slave system. The instrument chassis provides a common platform for coupling surgical instruments and endoscope for introduction into an entry point on the simulated patient. In one embodiment, the entry point can be a mouth, where access to the throat or larynx is desired, the rectum where access to the gastrointestinal system, or, more particularly, to the colon, is desired, or previously-prepared or surgically created openings or orifices.

In one embodiment, the system can also include an instrument chassis having a proximal section and a distal section. The chassis supports an endoscope. Generally, the dimensions and shape of the chassis at its distal section are typically reduced compared to its proximal end, to minimize the volume of the surgical equipment near the surgical entry point. Instrument interfaces can be movably mounted to the proximal section of the instrument chassis. Surgical instruments can be mounted at the proximal end to the instrument interface. Surgical instruments can be mounted at its proximal end to the instrument interface. The interface drives movable components in the surgical instrument as described in U.S. Pat. No. 6,491,701 which is incorporated by reference herein, in its entirety. The interface drives the instrument in a similar way. The surgical instruments are also movably coupled to the distal section of the chassis. The instrument interfaces are mounted to the proximal section of the chassis such that rotational and linear motion is permitted. Specifically, an instrument interface mounting or a flexible instrument shaft permits a pitch motion of the instrument interfaces relative to the chassis, a yaw motion of the instrument interfaces relative to the chassis and an insertion sliding motion of the instrument interfaces relative to the chassis. The system can function in a manner similar to the manner in which chopsticks operate, in that small motions at the proximal end of the tool, near a pivot location, can correspond to larger motions at the distal end of the tool for manipulating objects.

An actuation system operates the components of instrument, such as an end effector and various wrist joints. An actuation system operates the components of instrument, such as an end effector and various wrist joints. The actuation systems can include motors, actuators, drive systems, control systems, and other components for effecting controlling the instruments. An interface actuation system controls the movement of the instrument with respect to the chassis, and an interface actuation system controls the movement of the instrument with respect to the chassis. The surgical system can be configured to manipulate one, two, or more instruments.

Some robotic surgery systems use a surgical instrument coupled to a robotic manipulator arm and to an insertion linkage system that constrained motion of the surgical instrument about a remote center of motion aligned along the shaft of the surgical instrument and coincident with a patient entry point, such as an entry incision. Further details of these methods and systems are described in U.S. Pat. Nos. 5,817,084 and 6,441,577, which are incorporated by reference herein in their entirety.

Actuators can be operably coupled to interface discs. A more detailed description of the interface discs and their function in driving a predetermined motion in an attached surgical instrument is fully described, for example, in U.S. Pat. No. 7,963,913, filed Dec. 10, 2006, disclosing "Instrument Interface of Robotic Surgical System," which is incorporated by reference herein in its entirety.

Various embodiments of surgical instruments, end effectors, and wrist mechanisms are explained in detail in U.S. Pat. Nos. 5,792,135; 6,331,181; and 6,817,974, which are incorporated by reference herein in their entirety.

Switching from Robotic Surgery to Manual Surgery

One drawback of using robotic surgery is that instruments may need to be quickly removed when there is a "bleeder." Conventional surgical techniques may be required to find the source of the bleed, and close the bleed, before the rest of the surgical procedure can be performed. This can be difficult to practice, as it can be difficult to pre-program when a bleed will occur.

In one aspect of the invention, one or more of the tissues, organs, or organ blocks described herein includes a clot formed using animal blood, human blood, or the artificial blood compositions described herein and a clotting agent. The clot is dissolved during the simulated surgical procedure when the blood compositions, which, in this embodiment, contain an anti-clotting agent, are in sufficient contact with the clot to dissolve the clot. In another aspect of the invention, an anti-clotting agent is introduced, for example, into an IV bag, to cause the clot to dissolve.

When the clot dissolves, the surgeon using a robotic surgical apparatus either has to fix the resulting "bleeder" using the robotic surgical apparatus, or remove the apparatus from the patient, and go in manually to fix the bleeder.

Accordingly, in this embodiment, the simulated surgical systems can provide a more realistic experience than those in which there is never the possibility of having a bleeder.

VI. Kits

In another embodiment, the invention described herein relates to kits for use in simulated surgical procedures. In one aspect of this embodiment, the kits include the artificial blood compositions and one or more isolated tissues, organs, or organ blocks, which can be from cadavers, animals, or synthetic sources.

In one aspect of this embodiment, the tissue, organs, or organ blocks include a clot, formed by cutting the tissue, organs, or organ blocks, and forming a clot using either blood or the blood composition described herein, and a clotting agent. The kits can further include an anti-clotting agent, such as an amylase or protease, to dissolve the clot and start the flow of blood through the cut. The kits can also include a vasodilator, which can be present in the blood composition itself, to offset the vasoconstriction that occurs in animal tissue, organs, or organ systems when they are stored at cold temperatures.

In another aspect of this embodiment, the kits include a blood composition as described herein, which includes an anti-clotting agent, and tissue, organs, or organ blocks which include a clot.

In another aspect of this embodiment, the kits include a blood composition as described herein, and an anti-clotting agent.

All references referred to herein are hereby incorporated by reference for all purposes.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

The invention claimed is:

1. A kit comprising:
    i) a fake blood composition comprising: one or more colorants, one or more agents selected from the group consisting of proteins, urea, salts, buffers, and sugars, wherein the amount of salts, sugars, and proteins is selected to provide the composition with sufficient protein content to enable the blood to be clotted when clotting agents are used, and with an osmolality and osmolarity within 20% of that of human blood,
    ii) isolated tissue, organs, or organ systems derived from animal sources,
    wherein the tissue, organ, or organ system comprises animal blood, and has been modified by cutting the tissue, organ, or organ system, and preparing a "clot" using the animal blood and/or the fake blood composition, and a clotting agent selected from the group consisting of potato starch, corn starch, hydroxylethyl starch, and chitosan, and
    iii) a clot dissolving agent.

2. The kit of claim 1, wherein the clot dissolving agent is an enzyme selected from the group consisting of protease, amylase, and chitinase.

3. The kit of claim 1, wherein the clot dissolving agent is present in the fake blood composition.

\* \* \* \* \*